United States Patent
Modzelewski et al.

(10) Patent No.: US 6,979,571 B2
(45) Date of Patent: Dec. 27, 2005

(54) METHOD OF USING A PROTECTIVE TEST STRIP PLATFORM FOR OPTICAL METER APPARATUS

(75) Inventors: Brent Modzelewski, Brookfield, CT (US); George Rounds, Brookfield, CT (US)

(73) Assignee: Home Diagnostics, Inc., Ft. Lauderdale, FL (US)

( * ) Notice: Subject to any disclaimer, the term of this patent is extended or adjusted under 35 U.S.C. 154(b) by 0 days.

(21) Appl. No.: 10/208,878

(22) Filed: Aug. 1, 2002

(65) Prior Publication Data

US 2003/0026734 A1 Feb. 6, 2003

Related U.S. Application Data

(62) Division of application No. 09/448,711, filed on Nov. 24, 1999, now Pat. No. 6,458,326.

(51) Int. Cl.$^7$ ............................................. G01N 33/48
(52) U.S. Cl. ...................... 436/164; 436/169; 422/58; 422/61; 422/82.05
(58) Field of Search ..................... 422/58, 61, 68.1, 422/82.05; 436/164, 166, 169, 805

(56) References Cited

U.S. PATENT DOCUMENTS

| | | | |
|---|---|---|---|
| 2,297,248 | A | 9/1942 | Rudolph |
| 2,369,499 | A | 2/1945 | Treuhaft |
| 2,893,843 | A | 7/1959 | Adams |
| 2,893,844 | A | 7/1959 | Cook |
| 3,061,523 | A | 10/1962 | Free |

(Continued)

FOREIGN PATENT DOCUMENTS

| | | |
|---|---|---|
| AU | 45033/85 | 1/1986 |
| AU | 76758/87 | 2/1988 |
| CA | 1117784 | 2/1985 |
| CA | 1219797 | 3/1987 |
| DE | 34 39 181 | 10/1984 |

(Continued)

OTHER PUBLICATIONS

Kessler, G., et al., *Chem. Abstr.*, vol. 89, No. 13, p. 357 (1978).
Przybylowicz, E. P., et al., *Clinical Chemistry*, vol. 24, No. 6, p. 1108 (1978).
Reynolds, K. J. et al., *Brit. J. Anaesth.*, 67:638–643 (1991).
Adler, S. et al., *Advances in Automated Analysis*, vol. 1, pp. 421–424 (1971).
Adlercreutz, H. et al., *Clinical Chemistry*, vol. 21, No. 6, p. 676–684 (1975).
Al–Kaissi, E. et al., *Journal of Immunological Methods*, 58, pp. 127–132 (1983).
Article (ECRI): *Health Devices*, vol. 17, No. 9, pp. 253–271 (Sep. 1988).
Bandi, Z.L. et al., *Clinical Chemistry*, vol. 27, No. 1, pp. 27–34 (1981).

(Continued)

*Primary Examiner*—Lyle Alfandary-Alexander
(74) *Attorney, Agent, or Firm*—Finnegan, Henderson, Farabow, Garrett & Dunner, L.L.P.

(57) ABSTRACT

A test strip platform for a testing apparatus of the type using test strips, wherein the platform has a shroud defining a strip track for positioning an inserted strip over an optical aperture for making analytical determinations. The platform has a hood permanently mounted to the shroud for overlying the optical window and protecting the testing apparatus optics. The strip track has stabilizing members for holding the strip in testing position. The hood provides camming members for guiding the leading edge of an inserted strip into cooperative engagement with the stabilizing members for ensuring proper insertion of the strip.

5 Claims, 3 Drawing Sheets

U.S. PATENT DOCUMENTS

| | | |
|---|---|---|
| 3,092,465 A | 6/1963 | Adams |
| 3,099,605 A | 7/1963 | Free |
| 3,127,281 A | 3/1964 | Meyer |
| 3,232,710 A | 2/1966 | Rieckmann |
| 3,298,789 A | 1/1967 | Mast |
| 3,413,198 A | 11/1968 | Deutsch |
| 3,443,903 A | 5/1969 | Haack |
| 3,483,031 A | 12/1969 | Lauer |
| 3,501,009 A | 3/1970 | Jaworek |
| 3,506,126 A | 4/1970 | Serfass |
| 3,509,025 A | 4/1970 | Bergmeyer |
| 3,511,608 A | 5/1970 | Anderson |
| 3,552,925 A | 1/1971 | Fetter |
| 3,552,928 A | 1/1971 | Fetter |
| 3,560,161 A | 2/1971 | Webb |
| 3,577,162 A | 5/1971 | Gaehwiler |
| 3,591,480 A | 7/1971 | Neff |
| 3,593,568 A | 7/1971 | Schmitz |
| 3,604,815 A | 9/1971 | Clemens |
| 3,607,093 A | 9/1971 | Stone |
| 3,620,677 A | 11/1971 | Morison |
| 3,630,957 A | 12/1971 | Rey |
| 3,650,698 A | 3/1972 | Adler |
| 3,653,836 A | 4/1972 | Gruber |
| 3,658,480 A | 4/1972 | Kane |
| 3,660,638 A | 5/1972 | Oberli |
| 3,663,175 A | 5/1972 | Depositar |
| 3,672,838 A | 6/1972 | Trcka |
| 3,677,901 A | 7/1972 | Bergmeyer |
| 3,690,833 A | 9/1972 | Ferrari |
| 3,703,336 A | 11/1972 | Rosse |
| 3,709,612 A | 1/1973 | Clemens |
| 3,713,986 A | 1/1973 | Bergmeyer |
| 3,715,192 A | 2/1973 | Wenz |
| 3,718,439 A | 2/1973 | Rosse |
| 3,723,064 A | 3/1973 | Liotta |
| 3,748,044 A | 7/1973 | Liston |
| 3,762,609 A | 10/1973 | Hagen |
| 3,765,841 A | 10/1973 | Paulson |
| 3,769,178 A | 10/1973 | Rothermel |
| 3,775,058 A | 11/1973 | Bush |
| 3,775,595 A | 11/1973 | Rosse |
| 3,778,350 A | 12/1973 | Bergmeyer |
| 3,785,772 A | 1/1974 | Coggeshall |
| 3,791,933 A | 2/1974 | Moyer |
| 3,795,149 A | 3/1974 | Gillette |
| 3,795,484 A | 3/1974 | Daly |
| 3,798,004 A | 3/1974 | Zerachia |
| 3,802,843 A | 4/1974 | Kim |
| 3,804,593 A | 4/1974 | Smythe |
| 3,811,840 A | 5/1974 | Bauer |
| 3,814,582 A | 6/1974 | Rohrbaugh |
| 3,819,863 A | 6/1974 | Slaght |
| 3,822,285 A | 7/1974 | Werner |
| 3,837,339 A | 9/1974 | Aisenberg et al. |
| 3,847,553 A | 11/1974 | Verbeck |
| 3,853,472 A | 12/1974 | Rittersdorf |
| 3,864,166 A | 2/1975 | Barker |
| 3,876,374 A | 4/1975 | Burns |
| 3,881,992 A | 5/1975 | Raltson |
| 3,897,214 A | 7/1975 | Lange |
| 3,901,657 A | 8/1975 | Lightfoot |
| 3,902,052 A | 8/1975 | Amar |
| 3,907,503 A | 9/1975 | Betts |
| 3,910,701 A | 10/1975 | Henderson |
| 3,915,647 A | 10/1975 | Wright |
| 3,917,452 A | 11/1975 | Rittersdorf |
| 3,917,453 A | 11/1975 | Milligan |
| 3,919,051 A | 11/1975 | Koch |
| 3,926,736 A | 12/1975 | Bucolo |
| 3,929,581 A | 12/1975 | de Fonseca-Wollheimn |
| 3,933,593 A | 1/1976 | Sternberg |
| 3,936,357 A | 2/1976 | Milligan |
| 3,942,995 A | 3/1976 | Ichikawa |
| 3,950,133 A | 4/1976 | Monte |
| 3,954,342 A | 5/1976 | Boeke |
| 3,957,436 A | 5/1976 | Murray |
| 3,958,560 A | 5/1976 | March |
| 3,960,497 A | 6/1976 | Acord |
| 3,964,870 A | 6/1976 | Tiedemann |
| 3,971,630 A | 7/1976 | Sandrock |
| 3,973,129 A | 8/1976 | Blumberg |
| 3,973,189 A | 8/1976 | Angel |
| 3,975,398 A | 8/1976 | Werner |
| 3,979,274 A | 9/1976 | Newman |
| 3,980,437 A | 9/1976 | Kishimoto |
| 3,983,005 A | 9/1976 | Goodhue |
| 3,985,508 A | 10/1976 | Williams |
| 3,986,833 A | 10/1976 | Mast |
| 3,988,208 A | 10/1976 | Werner |
| 3,990,849 A | 11/1976 | Lee |
| 3,992,158 A | 11/1976 | Przybylowicz |
| 4,009,615 A | 3/1977 | Ruhl |
| 4,011,046 A | 3/1977 | Labes |
| 4,014,321 A | 3/1977 | March |
| 4,015,121 A | 3/1977 | Gagnon |
| 4,022,577 A | 5/1977 | Brooker |
| 4,038,485 A | 7/1977 | Johnston |
| 4,040,786 A | 8/1977 | Trivedi |
| 4,042,335 A | 8/1977 | Clement |
| 4,043,756 A | 8/1977 | Sommervold |
| 4,050,898 A | 9/1977 | Goffe |
| 4,056,468 A | 11/1977 | Breiter |
| 4,057,394 A | 11/1977 | Genshaw |
| 4,059,405 A | 11/1977 | Sodickson |
| 4,061,468 A | 12/1977 | Lange |
| 4,061,469 A | 12/1977 | DuBose |
| 4,066,362 A | 1/1978 | Carter |
| 4,066,403 A | 1/1978 | Bruschi |
| 4,068,169 A | 1/1978 | Angel |
| 4,069,017 A | 1/1978 | Wu |
| 4,076,502 A | 2/1978 | Dugle |
| 4,095,272 A | 6/1978 | Janzen |
| 4,098,574 A | 7/1978 | Dappen |
| 4,101,276 A | 7/1978 | Anderson |
| 4,109,159 A | 8/1978 | Onillon |
| 4,110,079 A | 8/1978 | Schaeffer |
| 4,125,327 A | 11/1978 | Margolis |
| 4,125,372 A | 11/1978 | Kawai |
| 4,128,628 A | 12/1978 | Brooker |
| 4,135,883 A | 1/1979 | McNeil |
| 4,144,306 A | 3/1979 | Figueras |
| 4,152,390 A | 5/1979 | Nosco |
| 4,153,668 A | 5/1979 | Hill |
| 4,160,646 A | 7/1979 | Furutani |
| 4,165,508 A | 8/1979 | Barter |
| 4,176,008 A | 11/1979 | Figueras |
| 4,178,153 A | 12/1979 | Sodickson |
| 4,180,060 A | 12/1979 | Kutter |
| 4,199,260 A | 4/1980 | Kusnetz |
| 4,199,261 A | 4/1980 | Tidd |
| 4,211,845 A | 7/1980 | Genshaw |
| 4,217,107 A | 8/1980 | Saito |
| 4,218,144 A | 8/1980 | Whitehouse |
| 4,219,529 A | 8/1980 | Tersteeg |
| 4,224,032 A | 9/1980 | Glover |
| 4,226,537 A | 10/1980 | Colley |
| 4,230,456 A | 10/1980 | Wu |
| 4,233,029 A | 11/1980 | Columbus |
| 4,238,196 A | 12/1980 | Acuff |
| 4,240,912 A | 12/1980 | Stumpf |

| | | |
|---|---|---|
| 4,253,846 A | 3/1981 | Smythe |
| 4,254,083 A | 3/1981 | Columbus |
| 4,255,384 A | 3/1981 | Kitajima |
| 4,255,788 A | 3/1981 | Schwartz |
| 4,256,693 A | 3/1981 | Kondo |
| 4,257,862 A | 3/1981 | Schnipelsky |
| 4,258,001 A | 3/1981 | Pierce |
| 4,261,041 A | 4/1981 | Starr |
| 4,269,938 A | 5/1981 | Frank |
| 4,272,482 A | 6/1981 | Jessop |
| 4,273,868 A | 6/1981 | Walter |
| 4,274,832 A | 6/1981 | Wu |
| 4,276,051 A | 6/1981 | Ginsberg |
| 4,277,561 A | 7/1981 | Monget |
| 4,278,439 A | 7/1981 | White |
| 4,281,062 A | 7/1981 | Kallis |
| 4,283,383 A | 8/1981 | Masson |
| 4,283,491 A | 8/1981 | Dappen |
| 4,288,228 A | 9/1981 | Oberhardt |
| 4,292,272 A | 9/1981 | Kitajima |
| 4,297,238 A | 10/1981 | Vormbrock |
| 4,298,345 A | 11/1981 | Sodickson |
| 4,298,688 A | 11/1981 | Kallies |
| 4,299,916 A | 11/1981 | Litman |
| 4,300,906 A | 11/1981 | Negersmith |
| 4,302,420 A | 11/1981 | Jakubowicz |
| 4,303,406 A | 12/1981 | Ross |
| 4,303,408 A | 12/1981 | Kim et al. |
| 4,303,753 A | 12/1981 | Lam |
| 4,308,485 A | 12/1981 | Ignazio |
| 4,310,399 A | 1/1982 | Columbus |
| 4,312,834 A | 1/1982 | Vogel |
| 4,318,984 A | 3/1982 | Magers |
| 4,318,985 A | 3/1982 | Bauer |
| 4,325,910 A | 4/1982 | Jordan |
| 4,330,299 A | 5/1982 | Cerami |
| 4,336,330 A | 6/1982 | Bauer |
| 4,337,065 A | 6/1982 | Hiratsuka |
| 4,338,279 A | 7/1982 | Orimo |
| 4,340,669 A | 7/1982 | Bauer |
| 4,353,983 A | 10/1982 | Siddiqi |
| 4,353,984 A | 10/1982 | Yamada |
| 4,361,648 A | 11/1982 | Shuenn-tzong |
| 4,363,874 A | 12/1982 | Greenquist |
| 4,366,061 A | 12/1982 | Papanek |
| 4,366,241 A | 12/1982 | Tom |
| 4,370,983 A | 2/1983 | Lichtenstein |
| 4,373,818 A | 2/1983 | Yamamoto |
| 4,384,042 A | 5/1983 | Miike |
| 4,390,343 A | 6/1983 | Walter |
| 4,390,621 A | 6/1983 | Bauer |
| 4,391,905 A | 7/1983 | Bauer |
| 4,391,906 A | 7/1983 | Bauer |
| 4,399,099 A | 8/1983 | Buckles |
| 4,403,984 A | 9/1983 | Ash |
| 4,407,959 A | 10/1983 | Tsuji |
| 4,415,700 A | 11/1983 | Batz |
| 4,418,037 A | 11/1983 | Katsuyama |
| 4,420,564 A | 12/1983 | Tsuji |
| 4,420,566 A | 12/1983 | Jessop |
| 4,427,632 A | 1/1984 | Okaniwa |
| 4,427,889 A | 1/1984 | Muller |
| 4,430,299 A | 2/1984 | Horne |
| 4,430,427 A | 2/1984 | Hopkins |
| 4,430,436 A | 2/1984 | Koyama |
| 4,448,207 A | 5/1984 | Parrish |
| 4,449,538 A | 5/1984 | Corbitt |
| 4,450,153 A | 5/1984 | Hopkins |
| 4,452,887 A | 6/1984 | Kitajima |
| 4,458,539 A | 7/1984 | Bilstad |
| 4,459,358 A | 7/1984 | Berke |
| 4,460,684 A | 7/1984 | Bauer |
| 4,464,172 A | 8/1984 | Lichtenstein |
| 4,472,498 A | 9/1984 | Masuda |
| 4,472,505 A | 9/1984 | Manabe |
| 4,476,222 A | 10/1984 | Ohtani |
| 4,477,575 A | 10/1984 | Vogel |
| 4,478,942 A | 10/1984 | Katsuyama |
| 4,478,944 A | 10/1984 | Gross |
| 4,483,924 A | 11/1984 | Tsuji |
| 4,492,462 A | 1/1985 | Pross |
| 4,499,052 A | 2/1985 | Fulwyler |
| 4,503,385 A | 3/1985 | Haynes |
| 4,503,555 A | 3/1985 | Brimhall, Jr. |
| 4,509,859 A | 4/1985 | Markart |
| 4,517,160 A | 5/1985 | Galle |
| 4,518,259 A | 5/1985 | Ward |
| 4,523,853 A | 6/1985 | Rosenbladt |
| 4,528,159 A | 7/1985 | Liston |
| 4,532,107 A | 7/1985 | Siddigi |
| 4,534,012 A | 8/1985 | Yokozawa |
| 4,540,670 A | 9/1985 | Arai |
| 4,547,460 A | 10/1985 | Eikenberry |
| 4,551,307 A | 11/1985 | Koyama |
| 4,552,458 A | 11/1985 | Lowne |
| 4,553,848 A | 11/1985 | Rosicke |
| 4,554,132 A | 11/1985 | Collins |
| 4,557,901 A | 12/1985 | Koyama |
| 4,562,148 A | 12/1985 | Sommer |
| 4,567,024 A | 1/1986 | Koyama |
| 4,576,793 A | 3/1986 | Koyama |
| 4,578,245 A | 3/1986 | Arai |
| 4,578,248 A | 3/1986 | Nagaoka |
| 4,587,100 A | 5/1986 | Amano |
| 4,587,220 A | 5/1986 | Mayambala-Mwanika |
| 4,592,365 A | 6/1986 | Georgi |
| 4,592,893 A | 6/1986 | Poppe |
| 4,594,224 A | 6/1986 | Okaniwa |
| 4,594,327 A | 6/1986 | Zuk |
| 4,595,562 A | 6/1986 | Liston |
| 4,602,995 A | 7/1986 | Cassaday |
| 4,603,428 A | 7/1986 | Sandrik |
| 4,604,254 A | 8/1986 | Yamamoto |
| 4,604,264 A | 8/1986 | Rothe |
| 4,604,579 A | 8/1986 | Cannon |
| 4,618,475 A | 10/1986 | Wang |
| 4,622,207 A | 11/1986 | Wang |
| 4,627,014 A | 12/1986 | Lo |
| 4,627,445 A | 12/1986 | Garcia |
| 4,632,559 A | 12/1986 | Brunsting |
| 4,637,403 A | 1/1987 | Garcia |
| 4,637,978 A | 1/1987 | Dappen |
| 4,642,286 A | 2/1987 | Moldowan |
| 4,647,430 A | 3/1987 | Zweig |
| 4,647,432 A | 3/1987 | Wakatake |
| 4,649,123 A | 3/1987 | Charlton |
| 4,661,319 A | 4/1987 | Lape |
| 4,668,619 A | 5/1987 | Greenquist |
| 4,669,878 A | 6/1987 | Meier |
| 4,670,218 A | 6/1987 | Gantzer |
| 4,671,937 A | 6/1987 | Katsuyama |
| 4,676,653 A | 6/1987 | Strohmeier |
| 4,685,059 A | 8/1987 | Yamamoto |
| 4,686,479 A | 8/1987 | Young |
| 4,687,329 A | 8/1987 | Schultz |
| 4,693,985 A | 9/1987 | Degen |
| 4,703,756 A | 11/1987 | Gough |
| 4,710,458 A | 12/1987 | Maines |
| 4,714,341 A | 12/1987 | Hamaguri |
| 4,717,546 A | 1/1988 | Barnett |
| 4,731,726 A | 3/1988 | Allen |
| 4,732,736 A | 3/1988 | Kobayashi |

| Patent No. | Date | Inventor |
|---|---|---|
| 4,734,360 A | 3/1988 | Phillips |
| 4,748,114 A | 5/1988 | Kallies |
| 4,772,561 A | 9/1988 | Genshaw |
| 4,773,097 A | 9/1988 | Suzaki |
| 4,774,192 A | 9/1988 | Terminiello |
| 4,775,637 A | 10/1988 | Sutherland |
| 4,780,283 A | 10/1988 | Meinecke |
| 4,782,511 A | 11/1988 | Nemec |
| 4,787,398 A | 11/1988 | Garcia |
| 4,790,979 A | 12/1988 | Terminiello |
| 4,791,461 A | 12/1988 | Kishimoto |
| 4,803,153 A | 2/1989 | Shibata |
| 4,803,159 A | 2/1989 | Smith-Lewis |
| 4,803,625 A | 2/1989 | Fu |
| 4,810,470 A | 3/1989 | Burkhardt |
| 4,814,142 A | 3/1989 | Gleisner |
| 4,816,224 A | 3/1989 | Vogel |
| 4,818,710 A | 4/1989 | Sutherland |
| 4,820,489 A | 4/1989 | Rothe |
| 4,820,649 A | 4/1989 | Kawaguchi |
| 4,824,639 A | 4/1989 | Hildenbrand |
| 4,839,297 A | 6/1989 | Freitag |
| 4,849,340 A | 7/1989 | Oberhardt |
| 4,855,108 A | 8/1989 | Masuda |
| 4,857,273 A | 8/1989 | Stewart |
| 4,866,836 A | 9/1989 | Von Brandt et al. |
| 4,870,005 A | 9/1989 | Akiyoshi |
| 4,876,204 A | 10/1989 | Inoue |
| 4,876,207 A | 10/1989 | Mack |
| 4,877,747 A | 10/1989 | Stewart |
| 4,889,131 A | 12/1989 | Salem et al. |
| 4,889,815 A | 12/1989 | Bradwell |
| 4,900,666 A | 2/1990 | Phillips |
| 4,909,260 A | 3/1990 | Salem et al. |
| 4,913,150 A | 4/1990 | Cheung et al. |
| 4,914,020 A | 4/1990 | Arai et al. |
| 4,929,561 A | 5/1990 | Hirschfeld |
| 4,931,384 A | 6/1990 | Layton et al. |
| 4,935,346 A | 6/1990 | Phillips |
| 4,937,050 A | 6/1990 | Meinecke et al. |
| 4,943,522 A | 7/1990 | Eisinger et al. |
| 4,949,400 A | 8/1990 | Leveen et al. |
| 4,950,454 A | 8/1990 | Masuda et al. |
| 4,952,373 A | 8/1990 | Sugarman et al. |
| 4,952,515 A | 8/1990 | Gleisner |
| 4,962,021 A | 10/1990 | Meserol et al. |
| 4,965,047 A | 10/1990 | Hammond |
| 4,970,172 A | 11/1990 | Kundu |
| 4,974,607 A | 12/1990 | Miwa |
| 4,976,724 A | 12/1990 | Nieto et al. |
| 4,981,779 A | 1/1991 | Wagner |
| 4,985,205 A | 1/1991 | Fritsche et al. |
| 4,987,085 A | 1/1991 | Allen et al. |
| 4,994,238 A | 2/1991 | Daffern et al. |
| 5,004,584 A | 4/1991 | Rayman |
| 5,019,574 A | 5/1991 | Miura et al. |
| 5,023,052 A | 6/1991 | Nagatomo et al. |
| 5,023,053 A | 6/1991 | Finlan |
| 5,029,583 A | 7/1991 | Meserol et al. |
| 5,035,863 A | 7/1991 | Finlan et al. |
| 5,036,852 A | 8/1991 | Leishman |
| 5,039,225 A | 8/1991 | Uekusa |
| 5,043,269 A | 8/1991 | Theodoropulos |
| 5,047,206 A | 9/1991 | Dombrowski |
| 5,047,213 A | 9/1991 | Finlan et al. |
| 5,047,351 A | 9/1991 | Makiuchi et al. |
| 5,049,487 A | 9/1991 | Phillips et al. |
| 5,055,265 A | 10/1991 | Finlan |
| 5,059,394 A | 10/1991 | Phillips et al. |
| 5,064,619 A | 11/1991 | Finlan |
| 5,067,093 A | 11/1991 | Przybylowicz et al. |
| 5,071,746 A | 12/1991 | Wilk et al. |
| 5,071,769 A | 12/1991 | Kundu |
| 5,079,174 A | 1/1992 | Buck et al. |
| 5,079,715 A | 1/1992 | Venkataraman et al. |
| 5,082,626 A | 1/1992 | Grage, Jr. |
| 5,096,809 A | 3/1992 | Chen et al. |
| 5,096,836 A | 3/1992 | Macho et al. |
| 5,104,619 A | 4/1992 | de Castro et al. |
| 5,104,793 A | 4/1992 | Buck |
| 5,104,811 A | 4/1992 | Berger et al. |
| 5,106,758 A | 4/1992 | Adler et al. |
| 5,110,550 A | 5/1992 | Schlipfenbacher et al. |
| 5,110,724 A | 5/1992 | Hewett |
| 5,114,350 A | 5/1992 | Hewett |
| 5,114,673 A | 5/1992 | Berger et al. |
| 5,116,763 A | 5/1992 | Greene et al. |
| 5,120,507 A | 6/1992 | Sano et al. |
| 5,124,128 A | 6/1992 | Hildenbrand et al. |
| 5,128,171 A | 7/1992 | Gleisner |
| 5,130,231 A | 7/1992 | Kennedy et al. |
| 5,130,258 A | 7/1992 | Makino et al. |
| 5,147,606 A | 9/1992 | Charlton et al. |
| 5,149,505 A | 9/1992 | English et al. |
| 5,152,962 A | 10/1992 | Lackie |
| 5,166,051 A | 11/1992 | Killeen et al. |
| 5,171,688 A | 12/1992 | Hewett et al. |
| 5,173,261 A | 12/1992 | Krause et al. |
| 5,174,963 A | 12/1992 | Fuller et al. |
| 5,179,005 A | 1/1993 | Phillips et al. |
| 5,183,741 A | 2/1993 | Arai et al. |
| 5,187,100 A | 2/1993 | Matzinger et al. |
| 5,188,966 A | 2/1993 | Eikmeier et al. |
| 5,188,968 A | 2/1993 | Kano et al. |
| 5,206,177 A | 4/1993 | DeLaCroix et al. |
| 5,207,263 A | 5/1993 | Maier et al. |
| 5,211,914 A | 5/1993 | Vogel et al. |
| 5,212,060 A | 5/1993 | Maddox |
| 5,215,716 A | 6/1993 | Arai |
| 5,217,691 A | 6/1993 | Greene et al. |
| 5,225,997 A | 7/1993 | Lederer et al. |
| 5,227,310 A | 7/1993 | Sakamoto et al. |
| 5,231,576 A | 7/1993 | Suzuki et al. |
| 5,246,858 A | 9/1993 | Arbuckle et al. |
| 5,251,126 A | 10/1993 | Kahn et al. |
| 5,252,293 A | 10/1993 | Drbal et al. |
| 5,279,294 A | 1/1994 | Anderson et al. |
| 5,281,395 A | 1/1994 | Markart et al. |
| 5,296,192 A | 3/1994 | Carroll et al. |
| 5,302,348 A | 4/1994 | Cusack et al. |
| 5,304,468 A | 4/1994 | Phillips et al. |
| 5,316,727 A | 5/1994 | Suzuki et al. |
| 5,321,492 A | 6/1994 | Detwiler et al. |
| 5,321,618 A | 6/1994 | Gessman |
| 5,339,821 A | 8/1994 | Fujimoto |
| 5,367,555 A | 11/1994 | Isoyama |
| 5,371,020 A | 12/1994 | Frischauf |
| 5,379,214 A | 1/1995 | Arbuckle et al. |
| 5,390,238 A | 2/1995 | Kirk et al. |
| 5,416,695 A | 5/1995 | Stutman et al. |
| 5,418,142 A | 5/1995 | Kiser et al. |
| 5,424,035 A | 6/1995 | Hones et al. |
| 5,424,545 A | 6/1995 | Block et al. |
| 5,431,880 A | 7/1995 | Kramer |
| 5,452,343 A | 9/1995 | Garland et al. |
| 5,453,360 A | 9/1995 | Yu |
| 5,462,051 A | 10/1995 | Oka et al. |
| 5,467,475 A | 11/1995 | Takahashi et al. |
| 5,470,752 A | 11/1995 | Burd et al. |
| 5,515,170 A | 5/1996 | Matzinger et al. |
| 5,518,689 A | 5/1996 | Dosmann et al. |
| 5,526,120 A | 6/1996 | Jina et al. |

| | | | | | |
|---|---|---|---|---|---|
| 5,529,755 A | 6/1996 | Higashio et al. | | FOREIGN PATENT DOCUMENTS | |
| 5,545,877 A | 8/1996 | Shelton | | | |
| 5,548,633 A | 8/1996 | Kujawa et al. | DE | 39 21 391 | 1/1991 |
| 5,554,531 A | 9/1996 | Zweig | EP | 0 095 057 | 11/1983 |
| 5,563,042 A | 10/1996 | Phillips et al. | EP | 0 110 173 | 6/1984 |
| 5,573,506 A | 11/1996 | Vasko | EP | 0 112 166 | 6/1984 |
| 5,576,952 A | 11/1996 | Stutman et al. | EP | 0 113 896 | 7/1984 |
| 5,579,001 A | 11/1996 | Dempsey et al. | EP | 0 133 481 | 2/1985 |
| 5,579,775 A | 12/1996 | Dempsey et al. | EP | 0 140 337 | 5/1985 |
| 5,581,369 A | 12/1996 | Righter et al. | EP | 0 141 648 | 5/1985 |
| 5,597,532 A | 1/1997 | Connolly | EP | 0 159 727 | 10/1985 |
| 5,605,150 A | 2/1997 | Radons et al. | EP | 0 166 878 | 1/1986 |
| 5,605,837 A | 2/1997 | Karimi et al. | EP | 0 169 055 | 1/1986 |
| 5,620,863 A | 4/1997 | Tomasco et al. | EP | 0 173 500 | 3/1986 |
| 5,622,429 A | 4/1997 | Heinze | EP | 0 174 247 | 3/1986 |
| 5,639,672 A | 6/1997 | Burd et al. | EP | 0 182 647 | 5/1986 |
| 5,666,404 A | 9/1997 | Ciccotelli et al. | EP | 0 183 524 | 6/1986 |
| 5,681,529 A | 10/1997 | Taguchi et al. | EP | 0 225 561 | 12/1987 |
| 5,695,949 A | 12/1997 | Galen et al. | EP | 0 256 806 | 2/1988 |
| 5,704,364 A | 1/1998 | Saltzstein et al. | EP | 0 271 854 | 6/1988 |
| 5,704,366 A | 1/1998 | Tacklind et al. | EP | 0 295 526 | 12/1988 |
| 5,715,823 A | 2/1998 | Wood et al. | EP | 0 336 483 | 10/1989 |
| 5,719,034 A | 2/1998 | Kiser et al. | EP | 0 345 781 | 12/1989 |
| 5,725,774 A | 3/1998 | Neyer | EP | 0 407 800 | 6/1990 |
| 5,728,352 A | 3/1998 | Poto et al. | EP | 0 414 563 | 2/1991 |
| 5,735,285 A | 4/1998 | Albert et al. | EP | 0 415 679 | 3/1991 |
| 5,745,308 A | 4/1998 | Spangenberg | EP | 0 473 241 | 3/1992 |
| 5,753,452 A | 5/1998 | Smith | EP | 0 475 692 | 3/1992 |
| 5,754,111 A | 5/1998 | Garcia | EP | 0 479 394 | 4/1992 |
| 5,755,942 A | 5/1998 | Zanzucchi et al. | EP | 0 511 120 | 10/1992 |
| 5,758,644 A | 6/1998 | Diab et al. | EP | 0 555 045 | 8/1993 |
| 5,762,871 A | 6/1998 | Neyer | EP | 0 574 134 | 12/1993 |
| 5,764,158 A | 6/1998 | Franklin et al. | EP | 0 735 369 | 3/1995 |
| 5,770,389 A | 6/1998 | Ching et al. | EP | 0 656 423 | 7/1995 |
| 5,770,839 A | 6/1998 | Ruebush et al. | EP | 0 759 555 | 8/1995 |
| 5,772,586 A | 6/1998 | Heinonen et al. | EP | 0 769 558 | 10/1995 |
| 5,772,963 A | 6/1998 | Cantatore et al. | EP | 0 779 367 | 12/1995 |
| 5,780,304 A | 7/1998 | Matzinger et al. | EP | 0 800 082 | 4/1996 |
| 5,782,878 A | 7/1998 | Morgan et al. | EP | 0 764 271 | 3/1997 |
| 5,785,650 A | 7/1998 | Akasaka et al. | EP | 0 779 984 | 6/1997 |
| 5,791,342 A | 8/1998 | Woodard | EP | 0 781 405 | 7/1997 |
| 5,795,543 A | 8/1998 | Poto et al. | EP | 0 781 406 | 7/1997 |
| 5,827,180 A | 10/1998 | Goodman | EP | 0 799 896 | 10/1997 |
| 5,837,546 A | 11/1998 | Allen et al. | EP | 0 816 849 | 1/1998 |
| 5,840,020 A | 11/1998 | Heinonen et al. | EP | 0 823 634 | 2/1998 |
| 5,841,846 A | 11/1998 | Abbruscato | EP | 0 823 635 | 2/1998 |
| 5,842,975 A | 12/1998 | Illyes et al. | EP | 0 823 636 | 2/1998 |
| 5,843,692 A | 12/1998 | Phillips et al. | EP | 0 826 777 | 3/1998 |
| 5,846,486 A | 12/1998 | Pugh | EP | 0 832 691 | 4/1998 |
| 5,850,320 A | 12/1998 | Warmka et al. | EP | 0 852 336 | 7/1998 |
| 5,866,349 A | 2/1999 | Lilja et al. | EP | 0 960 946 | 12/1999 |
| 5,872,627 A | 2/1999 | Miers | EP | 0 974 840 | 1/2000 |
| 5,885,839 A | 3/1999 | Lingane et al. | FR | 2191734 | 2/1974 |
| 5,922,530 A | 7/1999 | Yu | GB | 835551 | 5/1960 |
| 5,962,215 A | 10/1999 | Douglas et al. | GB | 911181 | 11/1962 |
| 5,968,760 A | 10/1999 | Phillips et al. | GB | 1037155 | 7/1966 |
| 5,986,754 A | 11/1999 | Harding | GB | 1485506 | 9/1977 |
| 5,989,917 A | 11/1999 | McAleer et al. | GB | 2029012 | 3/1980 |
| 5,995,236 A | 11/1999 | Roth et al. | GB | 2026160 | 6/1980 |
| 5,997,817 A | 12/1999 | Crismore et al. | GB | 2039035 | 7/1980 |
| 6,027,692 A | 2/2000 | Galen et al. | GB | 2090659 | 7/1982 |
| 6,032,352 A | 3/2000 | Furay et al. | JP | 49-11395 | 1/1974 |
| 6,040,195 A | 3/2000 | Carroll et al. | JP | 53-148522 | 12/1978 |
| 6,067,463 A | 5/2000 | Jeng et al. | JP | 54-113383 | 9/1979 |
| 6,084,660 A | 7/2000 | Shartle | JP | 55-136957 | 10/1980 |
| 6,168,957 B1 | 1/2001 | Matzinger et al. | JP | 55-155235 | 12/1980 |
| 6,193,873 B1 | 2/2001 | Ohara et al. | JP | 56-057937 | 5/1981 |
| 6,201,607 B1 | 3/2001 | Roth et al. | JP | 56-164941 | 12/1981 |
| 6,226,082 B1 | 5/2001 | Roe | JP | 56-168148 | 12/1981 |
| 6,233,471 B1 | 5/2001 | Berner et al. | JP | 57-101760 | 6/1982 |
| 6,268,162 B1 | 7/2001 | Phillips et al. | JP | 57-163848 | 10/1982 |
| | | | JP | 57-168144 | 10/1982 |

| | | |
|---|---|---|
| JP | 58-021544 | 2/1983 |
| JP | 59-032850 | 2/1984 |
| JP | 59-032851 | 2/1984 |
| JP | 59-108942 | 6/1984 |
| JP | 59-182347 | 10/1984 |
| JP | 60-091265 | 5/1985 |
| JP | 61-026842 | 2/1986 |
| JP | 61-068539 | 4/1986 |
| JP | 61-155849 | 7/1986 |
| JP | 61-292540 | 12/1986 |
| JP | 62-22066 | 1/1987 |
| JP | 62-298765 | 12/1987 |
| JP | 63-021558 | 1/1988 |
| JP | 63-175749 | 7/1988 |
| JP | 1-119743 | 1/1989 |
| JP | 7-311196 | 7/1995 |
| JP | 8-75735 | 3/1996 |
| SU | 172088 | 12/1965 |
| WO | 81/00622 | 3/1981 |
| WO | 81/00912 | 4/1981 |
| WO | 83/00931 | 3/1983 |
| WO | 84/02578 | 7/1984 |
| WO | 92/12428 | 7/1992 |
| WO | 92/15861 | 9/1992 |
| WO | 94/02578 | 2/1994 |
| WO | 96/07757 | 3/1996 |
| WO | 96/07892 | 3/1996 |
| WO | 96/07893 | 3/1996 |
| WO | 96/07907 | 3/1996 |
| WO | 96/07908 | 3/1996 |
| WO | 97/46878 | 12/1997 |
| WO | 99/46591 | 9/1999 |

OTHER PUBLICATIONS

Bell, P.M. et al., *British Medical Journal*, vol. 286, pp. 1230–1231, Apr. 16, 1983.
Billmeyer, F.W. Jr., et al., *Principles of Color Technology*, Second Edition, John Wiley & Sons, Inc. 1981.
Bio–Dynamics Corp., "Coagulation Unimeter CU500 Series Technical Service Manual," Nov., 1982.
Capaldi, Dante J. et al., *Analytical Biochemistry*, 129, 329–336 (1983).
Carrick, C.E., *Diabetes*, May 1990, vol. 39, Supp. 1, The Program for the 50th Annual Meeting of the American Diabetes Association in Atlanta, Georgia, Abstract #205.
Cate, J.C. IV, *Clinical Chemistry*, vol. 26, No. 2, p. 266 (1980).
Chance, B., *Rev. Sci. Instru.*, 22, pp. 634–638 (1951).
Chua, K.S., et al., *Clinical Chemistry*, vol. 24, No. 1, pp. 150–152 (1978).
Cohen, M. et al., *Med. J. Aust.* 1980; 2: 713–716.
Cohen, Matthew et al., *Med. J. Aust.* 1983; 2: 377–380.
Cowles, J.C., *Journal of the Optical Society of America*, vol. 55, No. 6, pp. 690–693, Jun. 1965.
Curme, H.G., et al., *Clinical Chemistry*, vol. 24, No. 8, pp. 1335–1342 (1978).
Damon Corporation, "Instrument Operating Parameters—Damon Microfluorometer," (no date available).
Davidson, J.A., et al., *Diabetes*, May 1990, vol. 39, Supp. 1, The Program for the 50th Annual Meeting of the American Diabetes Association in Atlanta, Georgia, Abstract #871.
De Pasqua, A., et al., *The Lancet*, p. 1165 (1984).
Driscoll, R.C., et al., *Clinical Chemistry*, vol. 29, No. 9, pp. 1609–1615 (1983).
Eastman Kodak Co., "DT60 Analyzer Operator's Manual," Pub. No. C–50, Part No. 632071, Jul. 1986.
Eastman Kodak Co., "Kodak Ektachem DT Slides: (GLU)—Glucose Test Methodology," Pub. No. C–300, Copyright 1986.
Eastman Kodak Co., "Kodak Ektachem DT Slides—Test Methodology—Glucose," Pub. No. C–300 (1992).
Eastman Kodak Co., "Normal Operation for the Kodak Ektachem DTSC Module," Pub. No. XP3100–5, Sep. 1991.
Elliott, R. J., *Physicians & Computers* vol. 2, No. 6, pp. 13–16 (1984).
European Patent Office Opposition File, European Patent 0 256 806, granted on Application No. 873–7014.8, Lifescan, Inc., Opposition by Boehringer Mannheim GmbH.
Evenson, M.A., et al., *Clinical Chemistry*, vol. 16, No. 7, pp. 606–611 (1970).
Fairclough et al., *Diabetes Care*, vol. 6, No. 1, pp. 45–49 (1981).
Feldman, J.M. et al., *Diabetes*, vol. 19, No. 5, pp. 337–343 (1970).
Finley, P.R. et al., *Clinical Chemistry*, vol. 24, No. 12, p. 2126 (1978).
Fleming, D.R., *Diabetes*, May 1990, vol. 39, Supp. 1, The Program for the 50th Annual Meeting of the American Diabetes Association in Atlanta, Georgia, Abstract #862.
Funnell, M.M., et al., *Diabetes*, May 1990, vol. 39, Supp. 1, The Program for the 50th Annual Meeting of the American Diabetes Association in Atlanta, Georgia, Abstract #200.
Geoghegan, W.D. in "Enzyme–Mediated Immunoassay," Ngo and Lenhoff, ed., pp. 451–465 (1985).
Geoghegan, W.D. et al., *Journal of Immunological Methods*, 60, pp. 61–68 (1983).
Gilden, J.L., et al., *Diabetes*, May 1990, vol. 39, Supp. 1, The Program for the 50th Annual Meeting of the American Diabetes Association in Atlanta, Georgia, Abstract #868.
Hahn B., et al., *Clinical Chemistry*, vol. 25, No. 6, pp. 951–959 (1979).
Hardin, E., et al., *Clinical Chemistry*, vol. 22, No. 4, pp. 434–438 (1976).
Havlin, C.E., et al., *Diabetes*, May 1990, vol. 39, Supp. 1, The Program for the 50th Annual Meeting of the American Diabetes Association in Atlanta, Georgia, Abstract #873.
"Healthcare Product Comparison System (HCPS): Blood Glucose Monitors," ECRI, 35 pp. (1999).
Ikeda, Y. et al., *Diabetologia*, 15, pp. 91–93 (1978).
Jarrett, L., et al., *Diabetes*, May 1990, vol. 39, Supp. 1, The Program for the 50th Annual Meeting of the American Diabetes Association in Atlanta, Georgia, Abstract #685.
Keilin, D., *Biochem.*, 42, pp. 221–229 (1948).
Kineiko, R.W., et al., *Clinical Chemistry*, vol. 29, No. 4, p. 688 (1983).
Lee, E.Y., et al., *Diabetes*, May 1990, vol. 39, Supp. 1, The Program for the 50th Annual Meeting of the American Diabetes Association in Atlanta, Georgia, Abstract #883.
Leroux et al., *Clin. Chem.*, vol. 34 No. 9, 1988, p. 1928.
Lo, D.H. et al, *Clinical Chemistry*, vol. 30, No. 6, p. 970 (1984).
Lo, D.H. et al., "Quantitative Estimate of Total Bilirubin in Serum Using the Kodak Ektachem Clinical Chemistry Slide (TBIL)," Jul. 31, 1984, (Copyright 1984 Eastman–Kodak). Medical Laboratory Automation Inc., "Pipette Care and Procedure Manual," (Copyright 1983).
Miles Laboratories, "Seralyzer Operating Manual," (Revised 1/84) including Test Module Inserts (Various revision dates) and Dilution System Instructions (Various revision dates).

Miles Laboratories, "Seralyzer Reflectance Photometer Assay Procedures in Brief" (Revised Aug. 1984).
Morgenstern, Stan et al., "STAC Rate Reaction and Fixed-Point Methods," pp. 16–22, Dec. 1976.
Morris, D.L. et al., *Biochem. J.*, vol. 147(3), pp. 593–603 (1975).
Murkin, S.A., et al, *Diabetes*, May 1990, vol. 39, Supp. 1, The Program for the 50th Annual Meeting of the American Diabetes Association in Atlanta, Georgia, Abstract #65.
Neeley, E. et al., "An Instrument for Digital Matrix Photometry," in Nipper, H. (ed), "Selected Papers on Clinical Chemistry Instrumentation", AACC Press, Washington, pp. 35–38 (1985).
Neeley, E. et al., "Reflectance Digital Matrix Photometry," in Nipper, H. (ed), "Selected Papers on Clinical Chemistry Instrumentation", AACC Press, Washington, pp. 39–42 (1985).
Neeley, W., et al., in Nipper, H. (ed), "Selected Papers on Clinical Chemistry Instrumentation", AACC Press, Washington, pp. 150–152, 153–156, 157–161 (1985).
Neely, W. et al., *Clinical Chemistry* 29/12, pp. 2103–2105 (1985).
Ngo, T.T., et al., *Analytical Biochemistry*, 105, pp. 389–397 (1980).
Ohkubo et al., *Clinical Chemistry*, vol. 27, No. 7, (1981) pp. 1287–1290.
Passey, R. et al., Clinical Chemistry, vol. 21, No. 11, pp. 1582–1584 (1975).
Passey, R., et al., Clinical Chemistry, vol. 21, No. 8, pp. 1107–1112 (1975).
Passey, R., et al., in Nipper, H. (ed), "Selected Papers on Clinical Chemistry Instrumentation", AACC Press, Washington, pp. 39–42 (1985).
Pellegrino, L.S., et al., Diabetes, May 1990, vol. 39, Supp. 1, The Program for the 50th Annual Meeting of the American Diabetes Association in Atlanta, Georgia, Abstract #882.
Percy–Robb, I.W., et al., Clinical Chemistry, vol. 24, No. 1, pp. 146–148 (1978).
Polesello A. et al., CRC Critical Reviews in Food Science and Nutrition 18(3):203–30 (1983).
Rachlin, J.A., et al., *Diabetes*, May 1990, vol. 39, Supp. 1, The Program for the 50th Annual Meeting of the American Diabetes Association in Atlanta, Georgia, Abstract #879.
Ratzlaff, K.L. et al., *Analytical Chemistry*, vol. 49, No. 14, pp. 2170–2176, (1977).
Richards, F.M. et al., *J. Mol. Biol.*, 37, pp. 231–233 (1968).
Rikmenspoel, Robert, *Applied Optics*, vol. 3, No. 3, pp. 351–355, (1964).
Schocken, D.M., et al., *Diabetes*, May 1990, vol. 39, Supp. 1, The Program for the 50th Annual Meeting of the American Diabetes Association in Atlanta, Georgia, Abstract #66.
Scott, W.E., *American Papermaker*, pp. 12–14, (May 1987).
Shibata, Shozo et al., *Analytica Chemica Acta*, 46, pp. 271–279 (1969).
Shirey, T.L., *Clinical Biochemistry*, vol. 16, No. 2, pp. 147–155, (1983).
Shoucri, R,M., et al., *Clinical Chemistry*, vol. 23, No. 9, pp. 1527–1530 (1977).
Smith, J., et al., in Nipper, H. (ed), "Selected Papers on Clinical Chemistry Instrumentation", AACC Press, Washington, pp. 193–197 (1985).
Sodickson, L., Presentation Slides (1976–1977).
Soloniewicz, R. et al., Institute of General Chemistry, Technical University, Lodz, Poland, pp. 105–114 (1980).
Songer, T.J., *Diabetes*, (May 1990), vol. 39, Supp. 1, The Program for the 50th Annual Meeting of the American Diabetes Association in Atlanta, Georgia, Abstract #210.
Sonksen, P.H. et al., *The Lancet*, vol. 1978:1, No. 8067, pp. 729–732 (1978).
Spayd, R.W., et al., *Clinical Chemistry*, vol. 24, No. 8, pp. 1343–1350 (1978).
Sternberg, J.C. et al., *Analytical Chemistry*, vol. 32, No. 1, Jan. 1960, pp. 84–90.
Sundaram et al., *Clinical Chemistry*, vol. 25, No. 8, (1979) pp. 1436–1439.
Table: *Clinical Chemistry*, vol. 27, No. 1, p. 33 (1981).
Tideman, A.M., *Diabetes*, (1990), vol. 39, Supp. 1, The Program for the 50th Annual Meeting of the American Diabetes Association in Atlanta, Georgia, Abstract #877.
Tietz, N. (ed.), Textbook of Clinical Chemistry, pp. 267–269 (1986).
Tietz, N.(ed.), Fundamentals of Clinical Chemistry, pp. 242–243 (1976).
TOA Technical Journal (1972) No. 3, pp2–9, "Royco–TOA Model 910 Cell Counter" (Japanese).
Toren, E.C. Jr., et al., *Clinical Chemistry*, vol. 16, No. 3, pp. 215–221 (1970).
Villeneuve, M.E. et al., *American Journal of Nursing*, , pp. 1258–1259 (1985).
Walford, S. et al., *The Lancet*, pp. 732–735, Apr. 8, (1978).
Walker, E.A., et al., *Diabetes*, (1990), vol. 39, Supp. 1, The Program for the 50th Annual Meeting of the American Diabetes Association in Atlanta, Georgia, Abstract #872.
Walter, B., *Analytical Chemistry*, vol. 55, No. 4, pp. 498A–514A (1983).
Wilkman, M.J., *Diabetes*, (1990), vol. 39, Supp. 1, The Program for the 50th Annual Meeting of the American Diabetes Association in Atlanta, Georgia, Abstract #682.
Wing, R.R., et al., *Diabetes Care*, vol. 9, No. 4, pp. 330–333 (1986).
Wylie–Rosett, J., et al., Brief Diabetes Quality Assurance (QA) Checklist,38 *Diabetes*, (May 1990), vol. 39, Supp. 1, The Program for the 50th Annual Meeting of the American Diabetes Association in Atlanta, Georgia, Abstract #866.
Zamzow, K., et al., *Diabetes*, (May 1990), vol. 39, Supp. 1, The Program for the 50$^{th}$ Annual Meeting of the American Diabetes Association in Atlanta, Georgia, Abstract #20.
Zimmet, P. et al., *Diabetes Research and Clinical Practice*, pp. 55–63 (1985).
Zollinger, H., Azo and Diazo, *Chemistry Allphatic and Aromatic Compounds*, pp. 243–248 (1961).

METHOD OF USING A PROTECTIVE TEST STRIP PLATFORM FOR OPTICAL METER APPARATUS

This is a division of application Ser. No. 9/448,711, filed Nov. 24, 1999 now U.S. Pat. No. 6,458,326, which is incorporated herein by reference.

TECHNICAL FIELD OF THE INVENTION

The invention relates generally to analyte determinations, more specifically to reflectance based optical monitoring systems, such as that employed in enzyme-based blood analyte chemistry analysis on disposable strips (e.g., blood glucose testing systems), and still more specifically to an apparatus for protecting the optics of such systems from contamination and ensuring proper strip insertion into a monitoring system.

BACKGROUND OF THE INVENTION

Portable analyte monitoring systems, including blood glucometers, are well known in the art. In the case of blood glucometers, these monitors are typically portable meter apparatus that are employed for personal monitoring of blood glucose levels, typically by diabetic patients. Since the 1970's, these devices have gained increasing popularity and acceptance for personal home use in managing when insulin injections are needed by diabetics. These meters have recently become increasingly portable, accurate and convenient due to advances in electronic, optical and test strip chemistry technologies.

The most common type of glucometer used today is based on reflectance optics in conjunction with a disposable, one-use test strip. In use, a small strip carrying reagent chemistry which reacts with blood is employed, such as that described in U.S. Pat. No. 5,296,192, the contents of which are hereby incorporated by reference herein. When fresh whole blood, typically from the lanced finger of a patient, is applied to the test strip, an enzyme-based reaction takes place producing a color change which typically progresses chromatically in proportion to the concentration of glucose present in the blood sample. After blood is applied and the reaction is underway, the strip is then inserted into the monitoring apparatus, and optical reflectance is used to measure the chromatic change. Once the apparatus has determined that the reaction is sufficiently complete, which optimally occurs when the reaction is stabilized, a reflectance measurement is converted through software in the monitoring apparatus into a glucose measurement, typically in mg/DI, and reported on a display to the user.

Such optical monitoring apparatus rely on proper insertion of the strip to ensure alignment of a portion of the strip containing the blood sample and reagent chemistry with the meter optics for accuracy. Further, if the optics become contaminated by blood or other foreign matter, accuracy is also compromised. Because these monitoring apparatus are used by diabetic patients, who frequently suffer sight and motor coordination impairment, it is important that the monitoring apparatus facilitates proper introduction and guided alignment of the strip, as well as protects the optics from contamination. Because of their portability, these apparatus will be subjected to various harsh environments and handling, which could contaminate the optics.

Prior art apparatus are inadequate for addressing these needs. One popular meter, sold under the name ONE TOUCH is described in U.S. Pat. No. 5,843,692. This device requires that the strip be first inserted into the meter and then blood is applied to the strip. This method is inconvenient for the user, as he or she must align a punctured finger with the test site on the strip while it resides in the meter. Consequently, this can result in the inadvertent spillage of blood onto the meter, and subsequently contaminate its optics. Frequently, this will occur when a large blood drop is deposited directly onto the strip. This device also utilizes a door to shield the optics from ambient light during use, which protects the optics when the meter is not in use. Unfortunately, this adds to the testing process the steps of opening and closing the door. Further, because the optical systems of this apparatus requires a door to block ambient light, breakage of the door renders the apparatus unusable.

SUMMARY OF THE INVENTION

There is a need in the art for a portable monitoring apparatus which will ensure proper strip alignment with its optics, and which will protect the optics from contamination.

The present invention relates to a method and apparatus for ensuring proper strip insertion into and alignment with an optical reflectance meter, while simultaneously protecting the optics of the meter.

According to one aspect of an illustrative embodiment of the invention, a test strip receiving member, or shroud, has an optical window which is disposed above the optics of the monitoring apparatus. A protective optics cover, or hood, is provided on the shroud to protect the optics underlying the optical window from contamination by foreign matter.

According to a further aspect of an illustrative embodiment of the invention, the shroud is provided with a track for guiding the strip to the testing position. The shroud provides fingers for engaging cooperative indents on the strip for tactile indication of proper testing position of the strip.

According to a further aspect of an illustrative embodiment of the invention, the protective hood is permanently mounted to the shroud and is provided with camming members for guiding the leading edge of an inserted strip such that it will be properly received by the fingers and directed into proper testing position.

These and other features and advantages of the present invention will be easily understood with reference to the Figures depicting an illustrative embodiment of the invention.

DETAILED DESCRIPTION OF AN ILLUSTRATIVE EMBODIMENT

Figure 1:
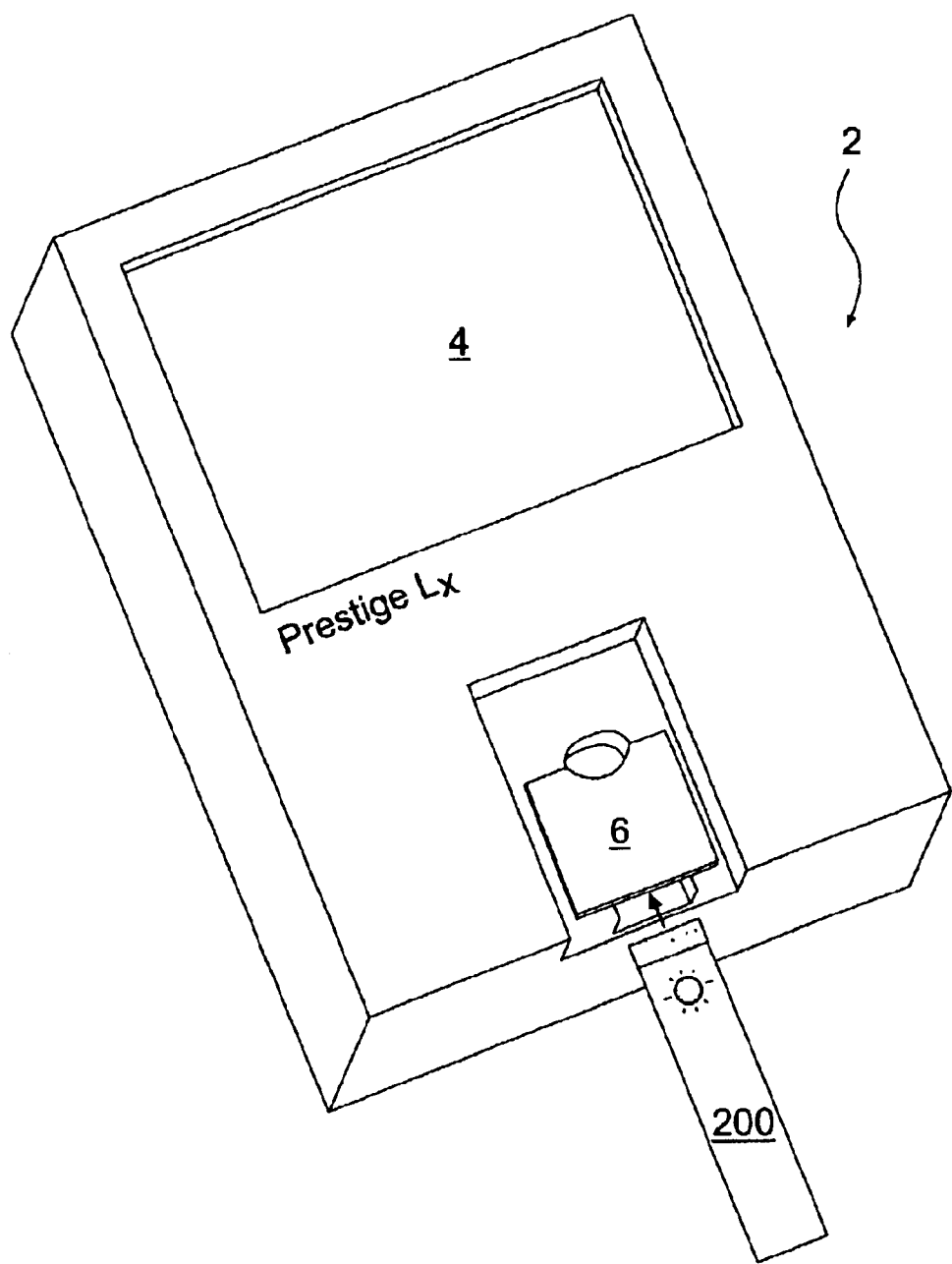
FIG. 1 is an isometric view of a portable monitoring apparatus with the inventive test strip platform of the present invention, depicting the insertion of a prior art test strip.

For the purposes of promoting an understanding of the principles of the invention, reference will now be made to an illustrative embodiment illustrated of the invention as depicted in the drawings.

Referring to FIG. 1, there is depicted a portable test apparatus 2, such as the type used to measure blood glucose in whole blood, available under the trade name PRESTIGE LX manufactured by Home Diagnostics, Inc. of Ft. Lauderdale, Fla. The housing of the apparatus contains microprocessor based electronics for computing blood glucose concentrations from a sample applied to a test strip 200. The apparatus 2 has a display 4, which may be an LCD display, for reporting calculations and other information to the user. The strip 200 is inserted into a strip-receiving platform 6, which will be discussed in greater detail hereinbelow.

Figure 2:
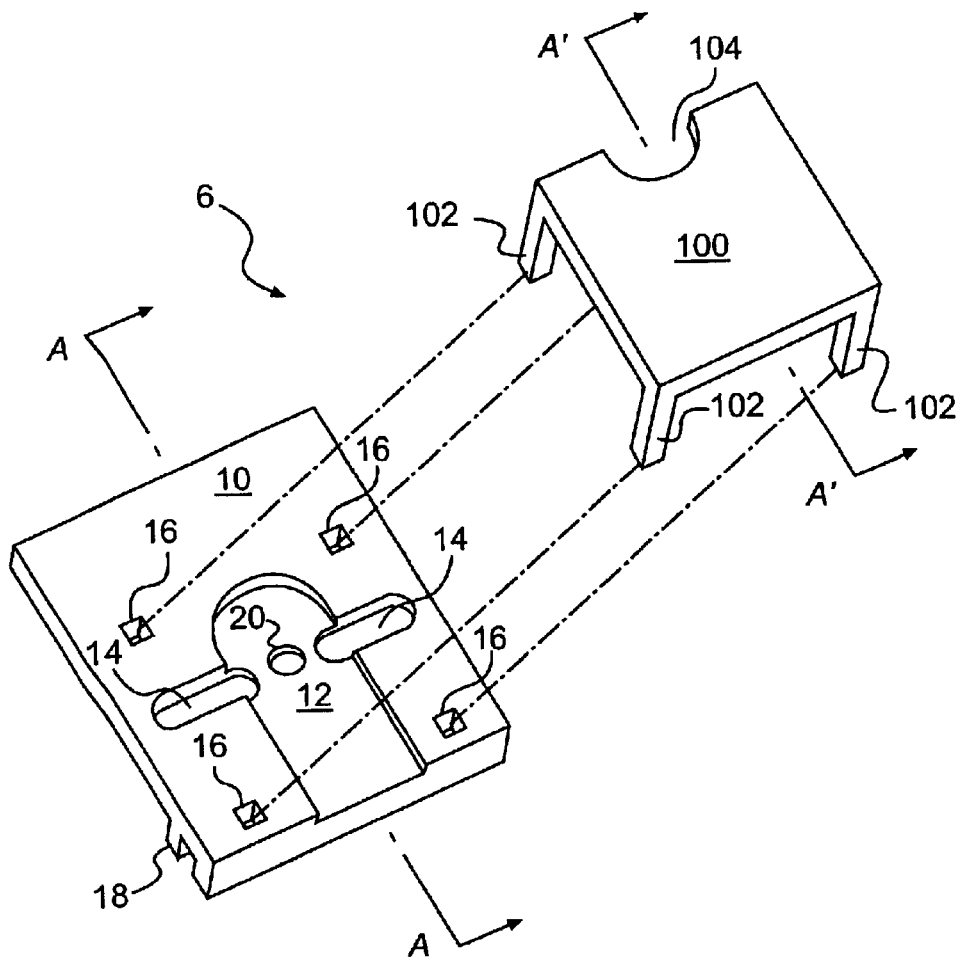
FIG. 2 is an isometric exploded view of an illustrative embodiment of a test strip platform according to the present invention.

FIG. 2 is an exploded view of the platform 6 shown in FIG. 1. The platform is removable from the apparatus 2 to facilitate cleaning to remove blood and other contaminants, and allows access to a window (not shown) which covers the optics of the apparatus. Removal of the platform 6 permits the optical window to be cleaned to ensure optimal performance of the apparatus 2. The platform 6 is comprised of two major components, which are permanently joined together. These components are the shroud 10 and the hood 100, which are discussed below in turn.

The shroud 10 receives the strip and guides it into position for the meter to operate properly. The shroud 10 has a cavity 12 which is lower than the top surface of the shroud and is dimensioned laterally to cooperatively receive a strip in snugly sliding, clearance fashion to ensure lateral stability while allowing advancement of the strip. On either side of the cavity 12 is a stabilizing member, or finger 14, which extends into the cavity diametrically opposed to an opposite finger. These fingers 12 bias a strip inserted into the cavity 12 into the proper position for the apparatus optics to make a good reading. When inserted, a strip will be snugly held against the bottom surface of the cavity 12 such that a color spot, described below, is held above an optical aperture 20. The optical aperture 20 is positioned above the optics of the apparatus when the platform 6 is secured in the meter apparatus 2. The shroud 10 also has means 16 for permanently attaching the hood thereto, and also means 18 for removably attaching the platform 6 to the meter apparatus housing.

The second major platform component is the hood 100, as further depicted in FIG. 2. The hood 100 serves to both protect the optics of the meter which underlie the optical aperture 20, and also to help guide a strip into proper testing position, as will be discussed hereinbelow. The hood has means 102 for permanently attaching it to the shroud 10. As depicted, means 102 on the hood mate with cooperating means 16 on the shroud for permanent mounting. These features as depicted are intended to be illustrative, and may take the form of any of a number of mechanical expedients and processes known in the art for rendering a permanent attachment between components, for example gluing, bonding, ultrasonic or RF welding, or very rigid mechanical locks or detents.

Figure 3:
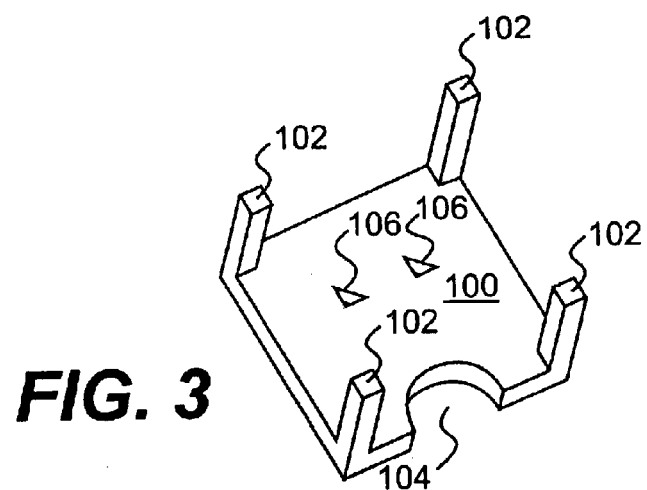
FIG. 3 is an isometric view of the bottom surface and camming members of the hood.

Turning to FIG. 3, the underside of the hood 100 is shown. A viewing notch 104 can be provided in order to allow the user to witness the advance of the leading edge of an inserted strip when the hood 100 is permanently attached to the shroud 10. Further provided are camming members 106, which provide a downward ramping surface for urging the leading edge of an inserted strip under the fingers 14 of the shroud when the hood 100 is permanently attached to the shroud 10. This feature will be further addressed with respect to FIG. 5, which is discussed after a brief description of a prior art strip shown in FIGS. 4A and 4B.

Figure 4A:
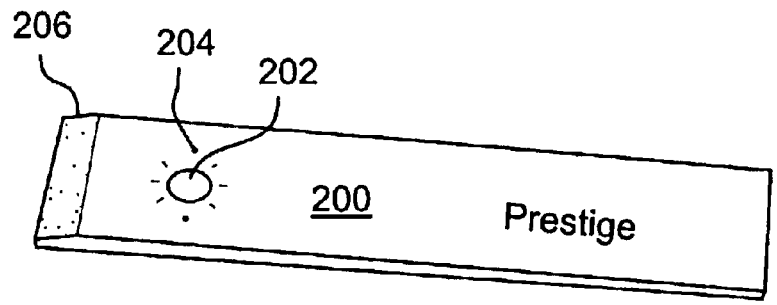
FIG. 4A is a top view of a prior art test strip.

Referring to FIG. 4A, the upper surface of a prior art test strip, such as that described in U.S. Pat. No. 5,296,192, is depicted. The strip 200 has a sample port or test spot 202, onto which blood is applied before introducing the strip into the apparatus 2. The strip 200 also has indents 204 or other surface feature which cooperate with the fingers 14. Of course, other cooperating structure can be provided in the platform to engage similar indents, which can be located anywhere on the strip. The indents provide a tactile guide for indicating when the strip has been inserted into the correct testing position (i.e., with the color spot as described below oriented over the optical aperture 20 of the shroud), and also provides a resistance for holding the strip in this position. The resistance is easily overcome by manually pulling on the strip, but is sufficient to retain the strip in the testing position if the meter is physically reoriented or jarred during testing. The strip 200 can also have a band 206 which can be used by the meter apparatus 2 to optically detect when the strip has been fully inserted. Full insertion usually indicates the testing position, and will correspond to the position where the indents 204 are engaged by cooperating structure such as those on fingers 14. The band 206 is also viewable through viewing notch 104 as seen in FIGS. 2 and 3 to allow the user to confirm that the strip has been inserted properly. As there is no band on the bottom side of the strip 200, the user can witness through the notch 104 whether the leading edge contains shows band 206 and thus whether the strip has been inserted properly.

Figure 4B:
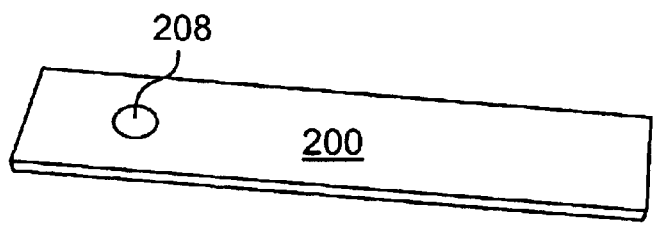
FIG. 4B is a bottom view of a prior art test strip.

FIG. 4B depicts the bottom surface of the strip shown in FIG. 4A. A viewing port or color spot 208 is located substantially directly beneath the test spot 204. When fluid containing analyte is applied to the test spot 202, it passes through an element containing chemistry in the strip producing a color change, which, if sufficient sample has been applied, can be visually verified by viewing the color spot 208 before inserting the strip 200 in the testing apparatus 2. The color spot 208, when the strip is inserted into the correct testing position is located over the optical aperture 20 in the shroud such that meter optics can access the color spot 208.

Figure 5:
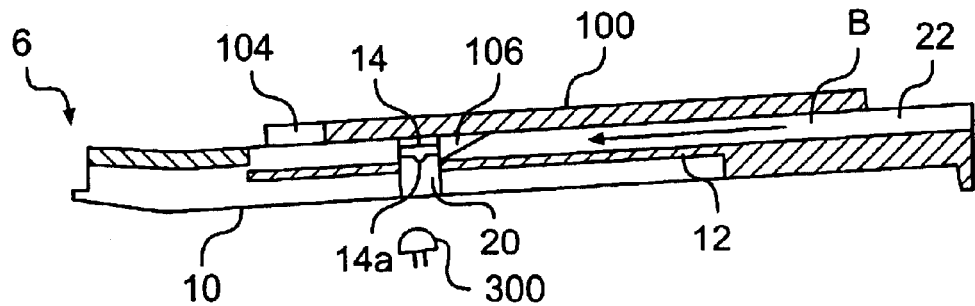
FIG. 5 is a cross sectional view of the shroud of FIG. 2 taken along line A—A with a cross sectional view of the hood taken along line A'—A' after permanent mounting of the hood on the shroud.

Turning now to FIG. 5, there is shown a cross sectional view of the platform 6, showing the shroud 10 and hood 100 permanently joined to each other. The cross sections of the shroud 10 and the hood 100 are taken along section lines A—A and A'—A' respectively. As can be seen, the cavity 12 of FIG. 1 corresponds to a strip track 22, wherein a strip may be inserted along the direction of arrow B. As can be appreciated, the leading edge of an inserted strip will encounter the camming members 106 and be deflected downwardly so that the leading edge passes beneath the fingers 14. As shown, protuberances 14a provide structures for cooperating with indents 204 in the prior art strip depicted in FIGS. 4A and 4B. As further shown, optical aperture 20 overlies meter optics 300, which are depicted in schematic form. As can be appreciated, the hood portion 100 of the platform protects the optics 300 from contamination.

While the invention has been illustrated and described in detail in the drawings and foregoing description, the same is to be considered as illustrative and not restrictive in character, it being understood that only an illustrative embodiment has been shown and described and that all changes and modifications that come within the spirit and scope of the invention are intended to be protected. For example, application of the present invention is not limited to optical reflectance meters or to meters which measure blood glucose levels, but will find application in any meter type which requires insertion of a test strip.

We claim:

1. A method of performing an analytical determination comprising the steps of:
   providing a testing apparatus comprising:
      a shroud portion, said shroud portion comprising a strip track, an optical aperture along said strip track, and at least one stabilizing member extending into said strip track in the vicinity of said optical aperture; and
      a hood portion immovably attached to said shroud portion over said strip track so as to protectingly overlie said optical aperture, said hood portion comprising at least one camming member descending into said strip track:
   providing a test strip having a leading edge and a color spot;
   applying a material containing analyte to said test strip so as to cause an optically measurable change at said color spot;
   introducing a said test strip into said strip track;
   advancing said test strip such that said at least one camming member and said at least one stabilizing member guide said test strip into a testing position; and
   while said test strip is in said testing position, optically accessing said color spot through said optical aperture to make the analytical determination.

2. The method of claim 1, further comprising the step of
   said at least one camming member downwardly deflecting said leading edge of said test strip so that said leading edge passes beneath said at least one stabilizing member.

3. The method of claim 1, wherein said test strip has at least one indent and said at least one stabilizing member has at least one protruberance engaging said at least one indent when said test strip is in said testing position.

4. The method of claim 3, further comprising the step of:
   said at least one protruberance engaging said at least one indent to provide a tactile indication when said test strip is inserted into said testing position.

5. The method of 3, further comprising the step of:
   said at least one protruberance engaging said at least one indent to provide a resistance for holding said test strip in said testing position.

* * * * *